US010123542B2

(12) United States Patent
Coats

(10) Patent No.: US 10,123,542 B2
(45) Date of Patent: Nov. 13, 2018

(54) COMPOSITIONS AND METHODS TO INCREASE PLANT YIELD

(71) Applicant: Coats Agri Aloe, LLC, Plano, TX (US)

(72) Inventor: Billy C. Coats, Garland, TX (US)

(73) Assignee: Coats Agri Aloe, LLC, Plano, TX (US)

( * ) Notice: Subject to any disclaimer, the term of this patent is extended or adjusted under 35 U.S.C. 154(b) by 0 days.

(21) Appl. No.: 15/229,969

(22) Filed: Aug. 5, 2016

(65) Prior Publication Data

US 2017/0035061 A1 Feb. 9, 2017

Related U.S. Application Data

(60) Provisional application No. 62/201,886, filed on Aug. 6, 2015.

(51) Int. Cl.
| | | |
|---|---|---|
| *A01N 65/42* | (2009.01) | |
| *C05B 17/00* | (2006.01) | |
| *C05G 3/00* | (2006.01) | |
| *A01N 65/00* | (2009.01) | |

(52) U.S. Cl.
CPC ............. *A01N 65/42* (2013.01); *A01N 65/00* (2013.01); *C05B 17/00* (2013.01); *C05G 3/00* (2013.01); *Y02A 40/143* (2018.01)

(58) Field of Classification Search
CPC .... A01N 2300/00; A01N 63/00; C05B 17/00; C05B 19/00; C05F 11/00; C05F 11/08; C05G 3/02
USPC ...................................................... 504/116.1
See application file for complete search history.

(56) References Cited

U.S. PATENT DOCUMENTS

| | | | |
|---|---|---|---|
| 4,039,470 A | 8/1977 | Kalmar | |
| 4,602,004 A | 7/1986 | Cohen | |
| 4,680,889 A | 7/1987 | Carlson | |
| 4,783,342 A | 11/1988 | Polovina | |
| 4,946,694 A | 8/1990 | Gunnerson et al. | |
| 4,966,892 A | 10/1990 | McAnalley | |
| 5,201,930 A | 4/1993 | Campbell | |
| 5,356,811 A | 10/1994 | Coats | |
| 5,922,774 A | 7/1999 | Winslow | |
| 6,013,259 A | 1/2000 | Pena | |
| 6,482,942 B1 | 11/2002 | Vittori | |
| 8,367,624 B2 | 2/2013 | Coats | |
| 9,622,488 B2 | 4/2017 | Coats | |
| 2004/0156920 A1 | 8/2004 | Kane | |
| 2004/0197364 A1 | 10/2004 | Brown | |
| 2006/0182775 A1 | 8/2006 | Everett | |
| 2007/0077262 A1 | 5/2007 | Scialdone | |
| 2008/0125320 A1* | 5/2008 | Coats .................. | A01N 3/00 504/116.1 |
| 2010/0154498 A1* | 6/2010 | Valencia ................ | C05D 9/02 71/23 |
| 2013/0102466 A1 | 4/2013 | Coats | |
| 2016/0015041 A1 | 1/2016 | Coats | |

FOREIGN PATENT DOCUMENTS

| | | | |
|---|---|---|---|
| AU | 2007319150 | | 11/2012 |
| CN | 102898223 | A | 1/2013 |
| CN | 102960160 | A | 3/2013 |
| DE | 19754206 | A1 | 6/1999 |
| DE | 19904801 | A1 | 8/2000 |
| ES | 2 234 431 | A1 | 6/2005 |
| JP | 59108702 | * | 6/1984 |
| JP | S59108702 | A | 6/1984 |
| JP | 61136583 | A | 6/1986 |
| JP | S61136583 | A | 6/1986 |
| WO | 199913717 | | 3/1999 |
| WO | 199913892 | | 3/1999 |
| WO | 2008061235 | A2 | 5/2008 |
| WO | 2015092719 | A1 | 6/2015 |
| WO | 2017024252 | A1 | 2/2017 |
| WO | 2017210768 | A1 | 12/2017 |

OTHER PUBLICATIONS

International Search Report and Written Opinion of the Korean Intellectual Property Office for PCT/US2016/045850 dated Nov. 18, 2016, 12 pp.
Sophia, Ochiki et al., "Effect of Aloe vera gel coating on postharvest quality and shelf life of mango (*Mangifera indica* L.) fruits Var. ngowe," Journal of Horticulture and Forestry, Jan. 2015, vol. 7, Article No. 13B4D5149545 (pp. 1-7).
Serrano, Maria et al., "Use of Aloe vera gel coating preserves the functional properties of table grapes," Journal of Agricultural and Food Chemistry, vol. 54, Issue 11, vol. 54, pp. 3882-3886.
CN102960160 Machine Translation Abstract, 1 pg.
International Search Report and Written Opinion for PCT/US2017/021411 dated Jun. 20, 2017, 14 pp.
"Aloe vera coating may prolong freshness, safety of fruits and vegetables," BrightSurf.com, accessed Feb. 7, 2006 at http://www.brightsurf.com/news/headlines/view.article.php?ArticleID=21057.
Extended European Search Report prepared by the European Patent Office for EP 07864543.9 dated Aug. 30, 2012, 12 pages.
International Search Report and Written Opinion for PCT/US2007/084998 dated Apr. 23, 2008.

(Continued)

*Primary Examiner* — Johann R Richter
*Assistant Examiner* — Danielle Sullivan
(74) *Attorney, Agent, or Firm* — Edwin S. Flores; Chalker Flores, LLP

(57) ABSTRACT

The present invention includes compositions and methods for increasing the absorption of nutrients by plants to increase their growth comprising: identifying a plant in need of enhanced nutrient uptake and growth when compared to non-treated plants; obtaining a whole leaf aloe vera extract and at least one plant nutrient selected from nitrogen (N), phosphorous (P), or potassium (K); and mixing the whole leaf aloe vera extract into a plant growth media, wherein the plant absorbs the one or more plant nutrients at a higher rate and the plants have at least one of increased growth, increased grain size, increased grain yield, increased panicles, or an increase in the number of seedlings per plant when compared to the addition of the one or more nutrients alone.

19 Claims, 2 Drawing Sheets

(56) References Cited

OTHER PUBLICATIONS

Martinez-Romero, et al., "Postharvest Sweet Cherry Quality and Safety Maintenance by Aloe Vera Treatment: A New Edible Coating," Postharvest Biology and Technology (2006), 39:93-100.

Valverde, J. M., et al., "Novel Edible Coating Based on Aloe vera Gel to Maintain Table Grape Quality and Safety," J Agric Food Chem (2005), 53:7807-7813.

XP002779996, Thomson Scientific, Abstract of CN20131010211, 2 pp.

XP002779997, Thomson Scientific, Abstract of JP19950282571, 10 pp.

XP002779998, Thomson Scientific, Abstract of JP19840259642, 8 pp.

XP002779999, Thomson Scientific, Abstract of CN20101272399, 4 pp.

Extended European Search Report prepared by the European Patent Office for EP 16833954.7 dated Apr. 12, 2018, 12 pages.

Material Safety Data Sheet for Sunland Aloe Vera Fertilizer, http://www.aloeverafertilizer.com/material-safety-data-sheet.html, printed Apr. 10, 2018, 3 pp.

* cited by examiner

US 10,123,542 B2

COMPOSITIONS AND METHODS TO INCREASE PLANT YIELD

CROSS-REFERENCE TO RELATED APPLICATIONS

This patent application is a non-provisional patent application of U.S. provisional patent application 62/201,886 filed on Aug. 6, 2015 and entitled "Compositions and Methods to Increase Plant Yield", which is hereby incorporated by reference in its entirety.

TECHNICAL FIELD OF THE INVENTION

The present invention relates in general to the field of treatments for plants, and more particularly, to compositions and methods for the treatment of plants to increase production.

BACKGROUND OF THE INVENTION

Without limiting the scope of the invention, its background is described in connection with the treatment of plants against pathogens.

In recent years, research and development efforts for the treatment of plant pathogens has focused on two main approaches, chemical and genetic. Over the years, more and more powerful chemical agents have been developed and refined to prevent and treat plants. These chemical agents are designed or isolated to affect a critical reproductive step in the growth, maturation or division of the target organism. However, more often than not, the chemical agent has an effect on other plants and animals.

Examples of methods for protecting fruits may be found in U.S. Pat. No. 4,946,694, issued to Gunnerson, et al., for a "Liquid coating for fruits." These inventors teach an improved coating for sticky fruits and a process for preparing such coated fruits. More particularly, the coating of the invention comprises a vegetable wax, a vegetable oil, a wetting agent and a protein. The process is said to include the steps of: (a) coating the fruit with a composition that includes a wetting agent and a suspension of a vegetable wax in a vegetable oil, (b) adding to the fruit a composition with a protein, (c) removing excess mixture from the fruit, and (d) drying the fruit. However, the addition of protein greatly increases the cost of the application and provides a potential substrate for attachment.

Yet another chemical coating is taught in U.S. Pat. No. 4,039,470, issued to Kalmar, entitled "Preservative coating for fruits and vegetables." This inventor coats fruits with a finely atomized spray of an acid solution of benzimidazole that must be retained in a separate corrosion resistant chamber prior to being mixed with the wax or resin solution just prior to application. However, unlike the teachings of this patent, the present invention does not have to be put into a corrosive chamber.

Yet another coating is taught in U.S. Pat. No. 4,783,342, issued to Polovina and entitled, "Polymeric film coating method for protecting plants, vegetables and fruit from drought," which relates to a method of preserving plants during periods of drought by applying a solid, water permeable film which controls water loss, to the surface of the plants. The same film can also be used to preserve vegetables and fruit. The water permeable film is also effective to preserve cut flowers.

Finally, U.S. Pat. No. 5,922,774, issued to Winslow teaches a method for controlling plant damage by insect herbivores. Briefly, this patent teaches using chemically-synthesized anthraquinones to repelling insect herbivores from plant surfaces and deterring them from feeding on plant surfaces by applying an aqueous dispersion of polycyclic quinone or precursor thereof to the foliage of the plant and/or to the surrounding soil in which the plant is rooted.

Despite the many efforts in this regard, nature finds a way to circumvent and select for those pathogens that are no longer resistant to the chemical or the genetic modification. Furthermore, these methods are most useful for those crops and plants that are replaced seasonally or yearly. Trees, plants and crops that live for many years before replacement, however, are unable to benefit from the genetic manipulation. Furthermore, many, many trees, plants and crops have not been able to be readily manipulated. These plants are still in need of protection and treatment from pathogens without an effect on the local environment, plants and fauna.

SUMMARY OF THE INVENTION

In one embodiment, the present invention includes a method for increasing the absorption of nutrients by plants to increase their growth comprising: identifying a plant in need of enhanced nutrient uptake and growth when compared to non-treated plants; obtaining a whole leaf aloe vera extract and at least one plant nutrient selected from nitrogen (N), phosphorous (P), or potassium (K); and at least one of mixing the whole leaf aloe vera extract into a plant growth media or spraying the whole leaf aloe vera extract on the plants, wherein the plant absorbs the one or more plant nutrients at a higher rate and the plants have at least one of increased growth, increased grain size, increased grain yield, increased yield, increased panicles, or an increase in the number of seedlings per plant when compared to the addition of the one or more nutrients alone. In one aspect, the aloe vera is a liquid, a gel, is dry, is ground, is freeze-dried, heat dried, vacuum dried, air-dried, spray-dried, or combinations thereof. In another aspect, the method further comprises adding to the whole leaf aloe vera extract at least one of a stabilizer, an anti-oxidant, a water-repellent, a UV absorbing agent, an anti-microbial agent, or combinations thereof. In another aspect, the whole leaf aloe vera extract is added to the plant growth medium or sprayed on the plant in situ. In another aspect, the whole leaf aloe vera extract is added to the plant growth medium or sprayed on the plant at 8, 16, 24, 32, 48, 72, 80, 88, 96, or 120 liters per 10,000 m$^2$. In another aspect, the aloe vera gel comprises an aloin content at least 600, 800, 1,000, 2000 ppm or more. In another aspect, the increase plant growth or yield is achieved without the addition of pesticides or insecticides. In another aspect, the plant comprises a grass, a grain, a fruit or a vegetable. In another aspect, the whole leaf aloe vera extract is diluted to 10, 9, 8, 7, 6, 5, 4, 3, 2, or 1% in a plant growth media or water prior to use. In another aspect, the plant growth media is selected from at least one of soil, nutrient enhanced soil, an in vitro growth media, hydroponic growth media, or agar growth media. In another aspect, the method further comprises reducing the amount of plant nutrients by 75, 50, or 25%, while still observing an increase in plant growth or yield. In another aspect, the plant is rice.

In another embodiment, the present invention includes a composition for treating a growth media for growing grass, fruits, vegetables that enhances nutrient uptake comprising: an aloe vera gel extract and one or more nutrients that are adapted for mixing into the growth media for grasses, fruits or vegetables and a reduced amount of plant nutrients, such that the plants have increased growth, increased grain size, increased grain yield, or an increase in the number of seedlings per plant when compared to the addition of the one or more nutrients alone. In another aspect, the aloe vera gel is concentrated, lyophilized, liquid, or gel. In another aspect, the composition further comprises at least one of a stabilizer, an anti-oxidant, a water-repellent, a UV absorbing agent, an anti-microbial agent, or combinations thereof. In another aspect, the aloe vera gel is dried, ground, whole or concentrated. In another aspect, the composition is at least one of repelling insects or pests without the addition of additional insecticides or pesticides.

Yet another embodiment includes a method for increasing the growth of a plant with a non-toxic, biodegradable composition comprising: identifying a plant growth media that is low in one or more nutrients; mixing into the plant growth media or spraying on the plant an aloe vera extract with the one or more nutrients that are missing from the plan growth media, such that the plants have increased growth, increased grain size, increased grain yield, increase in panicles, or an increase in the number of seedlings per plant, when compared to the addition of the one or more nutrients alone and without the need to treat the plants with an insecticide or a pesticide. In another aspect, the aloe vera extract is a liquid, gel, dry, ground, whole, freeze-dried, heat dried, vacuum dried, air-dried, spray-dried and combinations thereof. In another aspect, the method further comprises adding to the aloe vera extract at least one of a stabilizer, anti-oxidant, a water-repellent, a UV absorbing agent, an anti-microbial agent, or combinations thereof. In another aspect, the plant growth media, the aloe vera extract and the one or more nutrients are mixed or sprayed in situ. In another aspect, the plant comprises a fruit or vegetable and wherein the fruit or vegetable has an increase in the size and number of fruit or vegetable size, fruit or vegetable number and combinations thereof In another aspect, the plant comprises a grass, a grain, a fruit, a vegetable, or a tree. In another aspect, the aloe vera extract is added to the plant growth medium or sprayed on the plant at 8, 16, 24, 32, 48, 72, 80, 88, 96, or 120 liters per 10,000 m$^2$. In another aspect, the amount of N, P, or K fertilizer is decreased by 25, 50, or 75 percent, while still observing an increase in plant growth or yield as a result of the mixing or spraying of the aloe vera extract.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
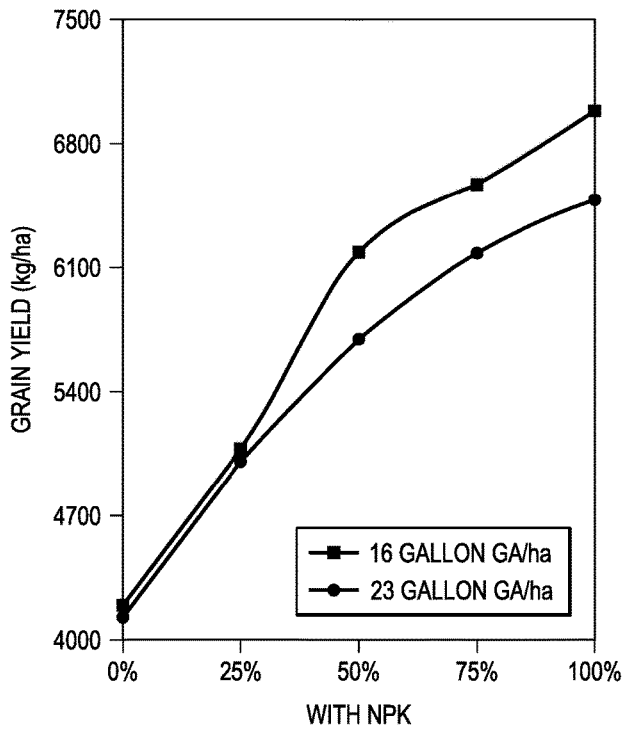
FIG. 1 shows the Ciherang grain yield (kg/ha) by administering GroAloe at different levels of NPK fertilization, KP.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Aloe vera, a tropical or subtropical plant of the genus Aloe has lance shaped leaves which contain a viscous but essentially clear gel which is given structural rigidity by hair-like connective fibers that run through it. The clear gel of the aloe vera is to be distinguished from the thick, mucilaginous yellow juice that occurs about the base of the plant leaves and adjacent the rind of the leaf. This juice, known as aloin, has been used for many years as an ingredient in many cathartics and purges. The aloin component of aloe vera includes, generally, several anthraquinones. The anthraquinones for use with the present invention may includes those from aloe, senna, rhubarb, and Cascara buckthorn, fungi, lichens, and insects.

Advantages of Coats Agri Aloe application. Aloe vera has shown in extensive laboratory studies to kill all bacteria, virus, fungus, yeast and mold it has been tested against. Importantly, after soaking the fruit, grain, grass, or vegetable in a solution of GroAloe (GroAloe is water soluble) it can be rinsed off the fruit, grain, grass, or vegetable with no side effects or toxicity. The present invention has a variety of uses, including: (1) increased moisture and nutrient uptake; (2) repels insects; (3) laboratory tested ability to kill bacteria, mold, yeast and fungus; (4) increase photosynthesis; (5) increase in plant production; (6) has no known toxicity after washing the plants, fruits, grasses or vegetables; and/or (7) does not harm the environment.

It is known that the therapeutic qualities of the clear gel of aloe vera leaves depend to a large extent on the freshness of the gel. For example, the pain of a jelly fish sting may be stopped not to recur by applying the clear gel from a leaf that has just been cut, but if the gel has been exposed to air and light for about one and a half hours, these powers are greatly diminished, if not lost. In some cases, however, relatively old unstabilized gel has been found to be effective and apparently the varying efficacy of a fresh gel for different medicinal purposes reflects the fact that the gel is a complex mixture of substances whose natural stability on exposure to air and light at different temperatures differ from batch to batch.

The raw material for preparing the cold process stabilized aloe vera gel (referred to GroAloe) is obtained from the leaves of fully mature aloe vera plants. For example, four to five year old plants are used to ensure full maturity to obtain a higher quality of leaves containing a larger amount of gel. The plants are grown under controlled conditions so that the size and structure of the leaves are more uniform, enabling accurate measurement and selection of quantities of materials to be used in the purification process.

Aloe vera leaves are processed as soon as possible after cutting from the plant. Immediate processing of the aloe vera leaves prevents degradative decomposition of the gel material as possible, which begins upon cutting due to natural enzymatic reactions as well as growth of bacteria within the gel due to the presence of oxygen. After cutting, the aloe vera leaves are washed in water or a water and detergent mixture. The leaves are then washed with a suitable bacteriocide and fungicide. For example, the leaves can be soaked in a water and chlorine solution for about 5 to 10 minutes, rinsed with sterilized water, and dried to limit any lint on the leaves.

The aloe vera gel is separated from the leaf by first slicing and grinding the leaves. The most common method of removing the gel from the rind is the hand-fillet method, although semi-automated and automated methods also exist. Any grinder known in the aloe vera art can be used. The clear aloe vera gel is then ground to form a gel that includes aloin. Often, the gel will include a solid phase or reticle, which is known as the leaf pulp. It has been found that any finisher known in the aloe vera arts can be used to separate the pure gel from the pulp. Briefly, the ground leaf mixture is fed into the finishing cavity, which is a space created by a spiral with specially designed flights and contained inside are a plurality of 360 degree cylindrical screens having openings on the order of one-quarter of an inch in diameter, to remove the large green pulpy portions, and ending with one having an opening on the order of 0.5 microns in diameter. As the spiral rotates, the more liquid phase of the ground leaf mixture is separated from the solid phase as the liquid phase migrates toward the area outside the screen. Once through the screen, the liquid phase flows into, e.g., a fully enclosed stainless steel pan. At this point, the aloe vera gel extract is generally clear yellow color in appearance. The yellow color is due to the presence of the aloin in the aloe vera mixture. Once separated from the liquid phase, the solid phase of the ground leaf mixture is discarded. This aloe vera gel is referred to herein as GroAloe. When the entire leaf is used to obtain the aloe vera gel extract, it is commonly referred to as whole leaf aloe vera gel or extract. Then only the gel is obtained (and the leaves discarded), then it is referred to as aloe vera gel. The whole leaf or the aloe vera gel extracts can be used in the present invention without further processing. For ease of transportation, it is possible to keep the gel in its original form, convert it into a dry, ground, freeze-dried, heat dried, vacuum dried, air-dried, spray-dried aloe vera gel (or combinations thereof). The aloe vera extract may also include one or more of a stabilizer, an anti-oxidant, a water-repellent, a UV absorbing agent, an anti-microbial agent, or combinations thereof. Often, the aloe vera gel or extract can be used in the plant growth medium or sprayed on the plant at 8, 16, 24, 32, 48, 72, 80, 88, 96, or 120 liters per 10,000 $m^2$. For example, mature plants are used to obtain a higher quality of leaves containing a larger amount of gel.

To the extent necessary, removal of bacteria, fungi and other organisms can be accomplished by using a combination of methods to assure that all bacteria are removed. This can include the use of chemical compounds such as glucose oxidase, boiling, ultraviolet light and the use of bacteria removing filters. In some embodiments, the aloe gel may also include additives or preservatives, e.g., sodium benzoate may be added in sufficient quantities to obtain a 0.1% solution of sodium benzoate in the final mixture. Another example of an additive may be a 0.1% solution of glucose oxidase/catalase. After addition of the additives, these may be incorporated into the gel using a mixer or blender and the components are mixed thoroughly for about 10 minutes. The gel is then allowed to sit for approximately 1 hour. To the extent needed, enough citric acid or other acid may be added to the gel to adjust the pH.

After treatment in this manner, the aloe vera composition may be concentrated by lyophilization with liquid nitrogen to a predetermined concentrate volume, if desired. It may then be transferred to amber bottles and kept in a cool place for future use. Or, as an alternative, it may be stored without such concentration in plastic-lined barrels.

The following example is set forth for the purpose of illustrating one embodiment of the present invention and is not to be interpreted as a limitation thereof or in any limiting fashion.

A series of tests were conducted on rice using GroAloe (whole leaf aloe vera extract or aloe vera gel) in various strength configurations in conjunction with NPK fertilizer Nitrogen (N), Phosphorus (P), and/or Potassium (K) at different dosage percentages. The information below summarizes the results.

Worldwide an average yield of rice per hectare per season is 4.7 metric tons (Central Research Institute for Food Crops) using chemical fertilizer and pesticides. Without using either NPK nutrients or GroAloe the average yield of the soil tested was only 4.03 metric tons per hectare. The soil tested were test plots at the Sukamandi Center for Rice Research.

Using 100% of the NPK dosage and a 4% dilution of GroAloe the yield increased to 6.97 metric tons per hectare, delivering an increase in production of 2.94 metric tons (6,479.76 lbs) per hectare (over there national average listed above). Based on the current Indonesian market (Index Mundi, March 2013) for white rice of $507.06 per metric ton, using GroAloe increased the revenue of each hectare by $1,151.02 USD or a 48% increase in yield.

GroAloe was tested at two strengths of dilution 6% and 4%. While both dilutions showed increases in production, generally, the lower 4% performed the best in every category with the NPK added.

GroAloe was found to be consistently effective for rice plants either with or without NPK fertilizer at different levels. Interestingly, the plants in the GroAloe treated soil were not attacked by pests or diseases, as there were no chemical insecticides or fungicides used on any plants during this test.

The plant growth media was an Ultisol soil type. The climate type was an Oldeman category E with long wet months and dry months (3 months, 4 months). The land was irrigated and located 15 m above sea level. The study was conducted using a randomized block design (Randomized Complete Block Design) with 3 replications. Treatments were tested for the provision of various doses of NPK fertilizer and spraying a solution of GroAloe at 4% or 6% diluted in water. In detail, the treatment being tested is as follows:

A. Without NPK fertilizer or GroAloe
B. 100% dose of N-P-K recommendation
C. Without fertilizer NPK+16 gallons GroAloe/ha
D. Without fertilizer NPK+23 gallons GroAloe/ha
E. 25% of the dose of N—P—K on +16 gallons GroAloe/ha
F. 25% of the dose of N—P—K on +23 gallons GroAloe/ha
G. 50% of the dose of N—P—K on +16 gallons GroAloe/ha
H. 50% of the dose of N—P—K on +23 gallons GroAloe/ha
I. 75% of the dose of N—P—K on +16 gallons GroAloe/ha
J. 75% of the dose of N—P—K on +23 gallons GroAloe/ha
K. 100% dose of NPK on +16 gallons GroAloe/ha
L. 100% dose of NPK on +23 gallons GroAloe/ha Giving 100% NPK fertilizers are: 335 kg/ha Phonska given 2 times (half at −2 days after planting (dap) and the second half at 30 dap, each half) and 165 kg/ha urea administered 2 times (half at 14 dap and the second half at 45 dap). While GroAloe given in 4 feedings with evenly sprayed on plants at 16, 30, 44 and 58 days after planting (dap).

The land was tilled and homogenized with a rotary plow (hand tractor), then plotted (creating the study plots) with irrigation channels and drainage. The study plot size was 6×5 $m^2$ plots bordered and framed 20-30 cm wide and 30 cm high. Each study plot had water channels in and out on their own in order to avoid mixing between study plots, while the replication study was limited by two bordered/blocked. After tilling, the fertilizer-soil conditions were maintained and left for 2 days before planting.

For comparison, 100% NPK fertilizers were as follows: 335 kg/ha Phonska given 2 times (−2 (day after planting) dap and 30 dap, each half), and 165 kg/ha urea administered 2 times (14 dap and 45 dap, each half). When used on the plants directly, GroAloe was added in 4 feedings with evenly sprayed on plants at 16, 30, 44 and 58 days after planting (dap).

The plants were trimmed at day 21 HST manually, grass/weeds removed and cleaned by hand, then cultivated free of weeds. While the control of pests and plant diseases are conventionally not done at all. It was found that GroAloe could control the pests and diseases of rice plants.

A Ciherang type of rice seed was planted rice at 16 days after moving to the plantation area made with the size of land 20 cm×20 cm, two seeds per planting hole. Data collected include:
(1) Analysis of the soil before the study by taking samples of soil in the study as much as 12 points and composited to analyze physical and chemical soil properties.
(2) The number of tillers and plant height at 16, 30, 44 and 58 dap, a sample of 12 clumps each study plot.
(3) The intensity of the green color of the leaves were observed using digital tools, SPAD-502, from the leaves clump samples.
(4) A day before harvest components observed results of 12 study plots in the form of clumps per panicle number, grain number (total, fill and empty) per hill, percentage of empty grain, moisture content of grain, and 1000 grain weight of grain fill.
(5) The grain was taken from 3×4 $m^2$ land and specified moisture content at harvest. Grain production is determined by Dry Milled Rice (MPD), the kg/ha.

Data obtained after being averaged and tabulated was analyzed using the Fingerprint Variety, while the difference between the average treatment was determined by Tukey's assay HSD (honestly significant difference) test at the 5% level. The relationship between the relevant variables was analyzed using correlation and regression techniques.

In general, the texture of the soil is dusty clay loam with a pH of 5.6 is rather sour. Low N content of 0.11%, as well as P205 and K20 is low). NPK fertilization was used to improve the growth and yield of rice plants.

Significant differences in plant height at 16 HST (days after planting) were only found between 100% NPK fertilizer recommendations without fertilization. Fertilizer plant height at 100% on 45-48 cm, whereas no fertilization at all at 39-40 cm. At 30 days after planting the height of the plants with 100% NPK ranged from 55-58 cm versus 50-51 cm without fertilization. At age 44 HST, a difference was seen for plant height between 100% fertilization and without fertilization, as well as the age of 58 HST. At the time of harvest a different plant height was observed when fertilizing at the 75% and 100% NPK dose recommendations. This suggests the need for NPK fertilizer for plant growth, since the soil had decreased levels of N, P and K. The average plant height was measured at 16, 30, 44, 58 HST (days after planting) and after harvest research conducted in Sukamandi.

TABLE 1

The average plant height aged 16, 30, 44, 58 HST (days after planting) and after harvest research in Sukamandi GroAloe, MH 2012/13.

| Treatment | Plant height (cm) | | | | |
|---|---|---|---|---|---|
| (NPK-GA) | 16 HST | 30 HST | 44 HST | 58 HST | PANEN |
| 0%-0 | 40.2 ab | 50.9 a | 67.5 abc | 86.1 abcd | 97.7 a |
| 100%-0 | 47.5 c | 55.5 abc | 82.1 dc | 98.8 ef | 110.0 cd |
| 0%-16 | 38.5 a | 50.1 a | 63.8 a | 78.1 a | 96.3 a |
| 0%-23 | 40.0 ab | 50.2 a | 65.1 ab | 81.1 ab | 96.7 a |
| 25%-16 | 40.2 ab | 51.3 a | 74.0 abcde | 89.0 bcde | 101.3 ab |
| 25%-23 | 41.4 abc | 51.7 a | 70.7 abcd | 84.0 abc | 102.0 abc |
| 50%-16 | 43.0 abc | 54.7 abc | 77.4 abc | 96.1 def | 107.3 abcd |
| 50%-23 | 41.4 abc | 52.3 a | 70.7 abcd | 87.5 abcd | 104.3 abcd |
| 75%-16 | 43.7 abc | 55.2 abc | 78.7 cde | 91.9 cdef | 108.7 bcd |
| 75%-23 | 44.6 abc | 55.4 abc | 75.7 bcde | 93.5 cdef | 108.0 bcd |
| 100%-16 | 45.5 abc | 58.2 c | 83.4 e | 100.2 f | 112.3 d |
| 100%-23 | 45.7 abc | 57.3 bc | 79.3 de | 96.2 def | 108.3 bcd |

The numbers in each column followed by the same letter, means not significantly different in the test HSD (honestly significant difference) 5%. Each figure in the table is an average of 36 times of observation.

At 16 days after transplanting (HST), without fertilizer NPK only obtained an average of 8 pups/clump. The real difference occurs only after the number of tillers 50% of NPK fertilizer recommendations. At 100% NPK fertilizer obtained on 11-13 tillers/clump. Generally rice seedlings grow until about 35-40 days after planting, and then decreased until harvest. At harvest time the number of tillers without NPK fertilization only 8-9 seedlings/family while in 100% NPK fertilizer obtained 11-12 tillers/clump (Table 2).

TABLE 2

The average number of chicks aged 16, 30, 44, and 58 DAP (days after planting) GroAloe research in Sukamandi, MH 2012/13.

| Treatment | Number of tillers/clump | | | |
|---|---|---|---|---|
| (NPK-GA) | 16 HST | 30 HST | 44 HST | Panen |
| 0%-0 | 8.1 ab | 10.0 a | 9.9 a | 97.7 a |
| 100%-0 | 10.9 c | 13.2 cde | 13.4 cde | 110.0 cd |
| 0%-16 | 8.0 a | 10.3 a | 10.5 ab | 96.3 a |
| 0%-23 | 8.1 ab | 10.3 a | 10.3 ab | 96.7 a |
| 25%-16 | 8.9 abc | 10.9 ab | 12.1 bc | 101.3 ab |
| 25%-23 | 9.3 abc | 11.7 abc | 12.3 bcd | 102.0 abc |
| 50%-16 | 10.3 bc | 12.8 bcde | 12.8 cde | 107.3 abcd |
| 50%-23 | 10.1 abc | 12.5 bcd | 12.5 cde | 104.3 abcd |
| 75%-16 | 11.0 cde | 13.4 cde | 13.4 cde | 108.7 bcd |
| 75%-23 | 10.7 cd | 13.2 cde | 13.8 cde | 108.0 bcd |
| 100%-16 | 13.0 e | 14.8 e | 14.5 e | 112.3 d |
| 100%-23 | 12.6 de | 14.1 de | 14.2 de | 108.3 bcd |

The numbers in each column followed by the same letter, means not significantly different in the test HSD (honestly significant difference) 5%. Each figure in the table is an average of 36 times of observation.

Cloroplast together with Chlorophyll pigments in the leaf cells play a role in the process of photosynthesis in which carbohydrates are made of $H_2O$ and $CO_2$. This causes green colored leaves. Therefore, the intensity of the green color indicates Chlorophyll present in leaves and observed using digital tools Soil and Plant Analyzer Development (SPAD) 502 Minolta. A SPAD value was measured between 16 and 58 days after planting are given in Table 3.

In general, leaf SPAD values decreased from 16 HST to 44 HST (stadia primordia), but at 58 HST (flowering stadia) the SPAD values increased, as shown in Table 3.

TABLE 3

The average age of the leaf SPAD values 16, 30, 44, and 58 HST (days after planting) GroAloe research in Sukamandi, MH 2012/13

| Treatment | Leaf SPAD value | | | |
|---|---|---|---|---|
| (NPK-GA) | 16 HST | 30 HST | 44 HST | 58 HST |
| 0%-0 | 38.17 a | 37.93 a | 32.47 a | 32.60 a |
| 100%-0 | 44.03 d | 44.93 b | 37.13 d | 42.13 de |
| 0%-16 | 38.90 ab | 37.70 a | 33.30 ab | 33.03 a |
| 0%-23 | 38.17 a | 37.97 a | 33.47 ab | 36.77 b |
| 25%-16 | 41.13 bc | 37.27 a | 33.67 abc | 39.30 bc |
| 25%-23 | 42.03 cd | 39.80 ab | 35.27 bcd | 38.97 bc |
| 50%-16 | 43.70 cd | 40.07 ab | 36.00 ab | 40.00 cd |
| 50%-23 | 42.60 cd | 38.73 a | 35.63 bcd | 40.87 cde |
| 75%-16 | 43.37 cd | 38.93 a | 36.00 cd | 42.07 de |
| 75%-23 | 44.30 d | 40.43 ab | 36.33 d | 40.90 cde |
| 100%-16 | 43.27 cd | 40.70 ab | 36.20 d | 41.23 cde |
| 100%-23 | 44.17 d | 40.37 ab | 37.57 d | 43.07 e |

The numbers in each column followed by the same letter, means not significantly different in the test HSD (honestly significant difference) 5%.

Without fertilizer NPK lowest grain yield, ranging between 4.03 and 4.20 t/ha and was not significantly different than 25% fertilization treatments with NPK fertilizer recommendations. At all levels of NPK fertilization applying with GroAloe does not significantly increase grain yield. Also adding of the concentration does not raise the grain yield using with GroAloe, even declining, when giving 16 gallons/ha increased to 23 gallons/ha.

Without adding 'GroAloe NPK a grain yield of 4.03 t/ha was found, and when administered GroAloe yielded 4.14 to 4.20 t/ha. Here the increase in yield by GroAloe was 110 to 170 kg/ha. When treating between 100%-0 (100% NPK fertilizer recommendations without GroAloe) a grain yield of 6.254 t/ha was obtained. At 75% NPK fertilization, a grain yield of 6.583 t/ha (with 16 gallons GroAloe/ha) and 6.185 t/ha (with 23 gallons of GroAloe/ha) was obtained (Table 4). This shows that giving GroAloe, especially 16 gallons GroAloe/ha, can replace 25% NPK fertilization.

TABLE 4

The average grain yield (t/ha DUP) and yield components at different levels of fertilization and giving GroAloe, research GroAloe in Sukamandi, MH 2012/13.

| Treatment | Result* | Malai/ | Grain/Clump | | Void-Grain | Weight Of 1000 seeds |
|---|---|---|---|---|---|---|
| (NPK-GA) | GKG (t/ha) | Clump | Total | Content | (%) | (g)* |
| 0%-0 | 4.029 a | 7.5 a | 829 ab | 640 ab | 22.64 a | 28.85 a |
| 100%-0 | 6.254 ef | 10.7 d | 1.282 d | 948 de | 26.11 a | 27.21 ab |
| 0%-16 | 4.201 abc | 8.2 ab | 759 a | 588 a | 22.27 a | 27.48 ab |
| 0%-23 | 4.144 ab | 7.7 a | 740 a | 591 a | 20.20 a | 27.16 ab |
| 25%-16 | 5.117 cd | 9.1 abcd | 909 abc | 708 abcd | 21.83 a | 27.59 ab |
| 25%-23 | 5.027 bcd | 8.5 abc | 906 abc | 700 abc | 22.72 a | 27.83 ab |
| 50%-16 | 6.197 ef | 10.2 bcd | 1.190 cd | 932 cde | 21.56 a | 27.60 ab |
| 505-23 | 5.707 de | 10.3 cd | 1.109 bcd | 853 bcde | 23.18 a | 27.33 ab |
| 75%-16 | 6.583 ef | 10.2 cd | 1.278 d | 981 e | 23.27 a | 27.56 ab |
| 75%-23 | 6.185 ef | 9.9 bcd | 1.133 bcd | 899 cde | 20.54 a | 27.87 b |
| 100%-16 | 6.966 f | 11.1 d | 1.411 d | 1.047 e | 25.73 a | 27.73 ab |
| 100%-23 | 6.478 ef | 10.8 d | 1.164 cd | 932 cde | 19.67 a | 27.98 b |

Numbers in each column followed by the same letter, means not significantly different in the test HSD (honestly significant different) 5%.
*At 14% grain moisture content At doses of NPK fertilizer 100% GroAloe provided increased grain yield. Without GroAloe a grain yield of 6.25 t/ha was obtained, whereas the addition of GroAloe gave a yield of 6.97 t/ha (16 gallons/ha) and 6.48 t/ha (23 gallons/ha); an increase in grain yield of 712 kg/ha and 224 kg/ha. With a fertilization of 25%, 50% and 75% NPK, GroAloe was added at 16 gallons/ha to 23 gallons. The increase in the highest yield with the addition of fertilizer GroAloe was obtained at 100% dosage. The administration of 16 gallons GroAloe/ha is equal to 712 kg/ha (11.38%), while the addition of 23 gallons GroAloe/ha increase in yield of only 224 kg/ha (3.58%). More specifically, the decline in the average grain yield at 23 gallons GroAloe/ha compared to 16 gallons/ha are given in Table 5. Under these conditions 23 gallons GroAloe/ha was excessive and caused a reduction in grain yield.

TABLE 5

The magnitude of the reduction of grain yield on giving 23 gallons GroAloe/ha compared to 16 gallons/ha, KP Sukamandi MH 2012/13.

| Fertilization with NPK | Grain yield Result (kg/ha) pada With GroAloe | | Decreasing Result Administered |
|---|---|---|---|
| | 16 gallon/ha | 23 gallon/ha | with 23 gallon GroAloe/ha (kg/ha) |
| Without | 4201 | 4144 | 57 |
| 25% recommended dose | 5117 | 5027 | 90 |
| 50% recommended dose | 6197 | 5707 | 490 |
| 75% recommended dose | 6583 | 6185 | 398 |
| 100% recommended dose | 6966 | 6478 | 488 |

Reduced grain yield by giving 23 gallons GroAloe/ha apparently consistent at all levels of NPK fertilizer, no fertilizer from 100% to fertilizer dosage recommendations. It is related to the concentration of administration may be too high on giving 23 gallons GroAloe/ha—concentration of 5.4% to 6.0%. While the provision of 16 gallons/ha yielded 4.0% (See Table 4).

Table 6 shows that increasing doses of NPK fertilization lead to reduced agronomic efficiency of fertilizer N when administering GroAloe, agronomic efficiency is shown for fertilizer 25%, 50%, 75% and 100%, respectively of 32-35, 27-34, 23-27 and 19-23 kg grain/kg N. At 100% NPK fertilization without GroAloe only 17.66 kg grain/kg N was obtained. But with 100% NPK fertilization, the addition of GroAloe gave an efficiency value of 23.31 N (16 gallons GroAloe/ha), 19.44 (23 gallons GroAloe/ha) kg grain/kg N. Thus, it was found that GroAloe improves agronomic efficiency of N, especially at 16 gallons GroAloe/ha.

TABLE 6

Grain yield and agronomic efficiency at different NPK fertilization and GroAloe, KP Sukamandi MH 2012/13.

| Treatment | | Grain Yield Result (kg/ha) | Grain Yield Result Over Control (kg/ha) | N Fertilizer (kg/ha) | AgronomiC N efficiency (k Grain/KG N) |
|---|---|---|---|---|---|
| NPK (%) | GroAloe (gallon/ha) | | | | |
| 0 | — | 4029 | — | — | — |
| 100 | — | 6254 | 2225 | 126.0 | 17.66 |
| 0 | 16 | 4201 | 172 | — | — |

TABLE 6-continued

Grain yield and agronomic efficiency at different NPK fertilization and GroAloe, KP Sukamandi MH 2012/13.

| Treatment | | Grain Yield Result (kg/ha) | Grain Yield Result Over Control (kg/ha) | N Fertilizer (kg/ha) | AgronomiC N efficiency (k Grain/KG N) |
|---|---|---|---|---|---|
| NPK (%) | GroAloe (gallon/ha) | | | | |
| 0 | 23 | 4144 | 115 | — | — |
| 25 | 16 | 5117 | 1088 | 31.5 | 34.54 |
| 25 | 23 | 5027 | 998 | 31.5 | 31.68 |
| 50 | 16 | 6197 | 2168 | 63.0 | 34.41 |
| 50 | 23 | 5707 | 1678 | 63.0 | 26.63 |
| 75 | 16 | 6583 | 2554 | 94.5 | 27.03 |
| 75 | 23 | 6185 | 2156 | 94.5 | 22.81 |
| 100 | 16 | 6966 | 2937 | 126.0 | 23.31 |

Interesting, it should also be noted that the 75% NPK fertilization and delivery of 16 gallons GroAloe/ha NPK fertilizer yields a savings of 25% in NPK fertilizer, at which time the N agronomic efficiency was 27.03 kg grain/kg N (Table 6).

The number of panicles formed on treatment without NPK fertilization yielded 7.5 to 8.2 panicles/clump. The number of panicles was significantly different when using NPK fertilizer at 50%, 75% and 100%, with 9.9 to 11.1 panicles/clump. Total amount of grain and grain content was also significantly different between no fertilizers and 50%, 75% and 100% NPK fertilizer (Table 4). The number of panicles using 16 gallons GroAloe was different from the 23 gallons GroAloe. At the same level of NPK fertilizer, the number of panicles was higher for 16 gallons GroAloe. A significant effect was found when giving GroAloe, yielding an increase in the total amount of grain and grain content/clump. In the control, treatment (without NPK and GroAloe) gained 829 total grains with 640 grain content/clump (Table 4). GroAloe using increasing doses from 16 to 23 gallons of GroAloe/ha gave a higher total grain and grain fill. The 100% NPK fertilization treatment only yielded 1282 total grain and 948 grain fill, but with GroAloe, 16 gallons/ha it increased to 1411 total grain and grain fill 1047/clump while giving GroAloe 23 gallons/ha only gave 1164 total grain and 932 grain content/clumps. Grain emptiness was not affected significantly by all treatments. But giving 16 gallons GA/ha NPK fertilizer 75% and 23 gallons GA/ha in 100% NPK fertilizer, an increase in grain fill and weight was observed (Table 4).

Giving GroAloe affected grain yield, at 100% dosage recommendation fertilizer NPK with GroAloe administration, particularly the 16 gallons GA/ha, an increase in grain yield of 712 kg/ha (11.38%) was observed, with an agronomic efficiency for fertilizer N that increased from 17.66 kg grain/kg N to 23.31 kg grain/kg N. Higher grain yield at 75% NPK fertilization and delivery of 16 gallons GA/ha grain yield (compared to 100% NPK fertilizers) was observed with the administration of 16 gallons GA/ha can replace the role of the 25% fertilizer NPK (84 kg and 41 kg Urea Phonska), increasing the agronomic efficiency of 25% N to 27.03 kg grain/kg N.

Another increase was found for GroAloe when looking at the total amount of grain and grain content/clump. Correlation matrix (Table 7) shows the greatest effect of GroAlo in grain yield with yield components, which showed a high correlation between grain yield with number of panicles/clump, total grain/cluster, and filled grain/cluster; respectively with a correlation coefficient 0.7616; 0.8676 and 0.8881. From FIG. 1 and FIGS. 2A to 2C it can be concluded that the distribution of the data is determined by grain yield over the total amount of grain and grain content of the form.

TABLE 7

Correlation matrix between grain yield with yield components of rice on NPK fertilizer research and GroAloe, KP Sukamandi MH 2012/13.

| | Grain Result | Malai/ Clump | Total Grain/ rpn | Grain content/ rpn | Emptiness (%) | Weight 1000 (g) |
|---|---|---|---|---|---|---|
| Grain | 1.0000 | — | — | — | — | — |
| Malai/ | 0.7616 | 1.0000 | — | — | — | — |
| Total Grain/rpn | 0.8676 | 0.8974 | 1.0000 | — | — | — |
| Grain content/rpn | 0.8881 | 0.8907 | 0.9819 | 1.0000 | — | — |
| Emtpiness (%) | 0.1549 | 0.3141 | 0.3855 | 0.2085 | 1.0000 | — |
| The Weight 1000 (g) | 0.4603 | 0.2075 | 0.2465 | 0.3018 | −0.1761 | 1.0000 |

FIG. 1 shows the Ciherang grain yield (kg I ha) by administering GroAloe at different levels of NPK fertilization, KP.

Figure 2A:
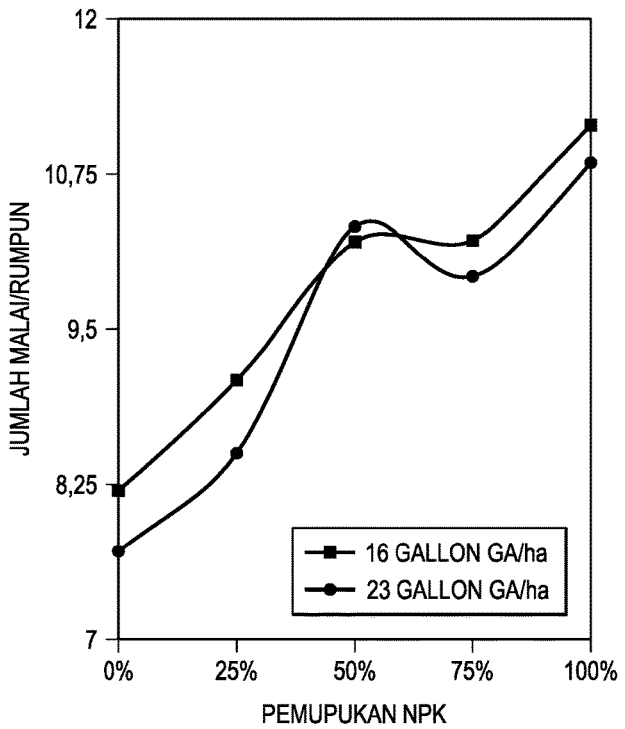
FIGS. 2A to 2C show the number of panicles/clump (FIG. 2A), the total amount of grain/cluster (FIG. 2B) and the number of filled grain/cluster (FIG. 2C) by administering GroAloe at different levels of NPK fertilization, KP Sukamandi MH 2012/13.
Figure 2B:
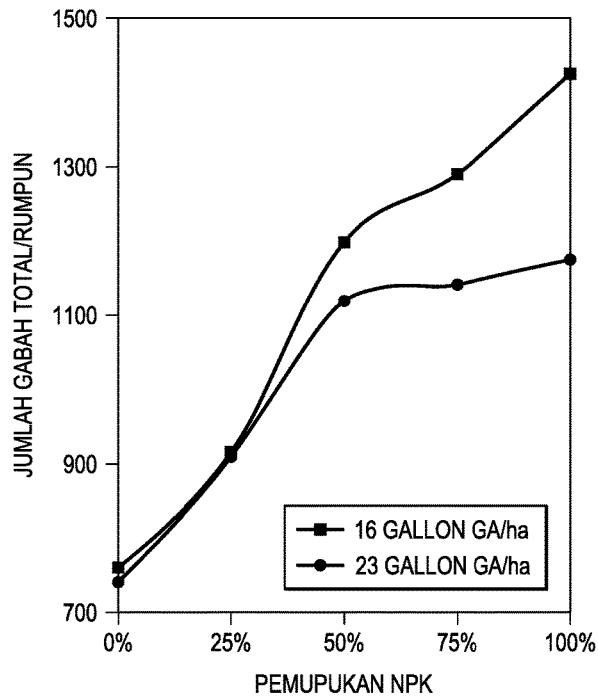
Figure 2C:
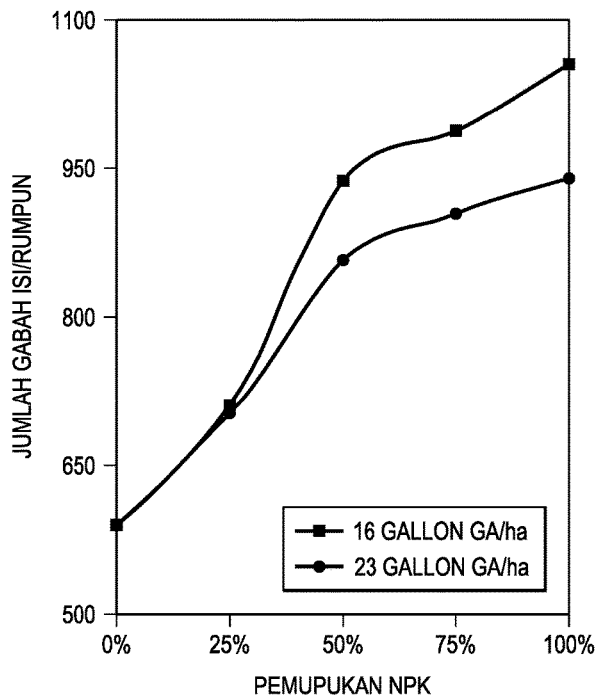

FIGS. 2A to 2C shows the number of panicles/clump (FIG. 2A), the total amount of grain/cluster (FIG. 2B) and the number of filled grain/cluster (FIG. 2C) by administering GroAloe at different levels of NPK fertilization, KP Sukamandi MH 2012/13.

TABLE 8

Summary of Soil Site Analysis

| Soil Characteristic | Value | Criteria | Analysis Method |
|---|---|---|---|
| Soil Texture | | Texture Class: | Pipette |
| Clay (%) | 40.0 | Clay | |
| Clay Dust (%) | 51.0 | Dust | |
| Sand (%) | 9.0 | | |
| pH $H_2O$ (1:2.5) | 5.6 | slightly acidic | pH meter |
| pH KCI (1:2.5) | 4.9 | Acidic | |
| N-total (%) | 0.11 | low | Micro Kjeldahl |
| C-organic (%) | 1.46 | low | Walkley & Black |
| C/N | 13.27 | Mediumg | |
| $P_2O_5$-potential (mg/100 g) | 38 | Medium | HCI 25% |
| $K_2O$ (mg/100 g) | 7 | Very low | HCI 25% |
| $P_2O_5$-Availability (ppm) | 4.7 | Low | Bray-1 |
| K-dd (cmol(+)/kg) | 0.06 | Very low | $NH_4OAc$ pH 7 |
| KTK (cmol(+)/kg) | 17.26 | low | $NH_4OAc$ pH 7 |

GroAloe was consistently effective in rice plants, either without fertilizer NPK or NPK fertilizer at different levels. The effectiveness of this material was optimum using 16 gallons GroAloe/ha, with an increase in grain yield by 712 kg I ha (11 increasing, 38%), while reducing the amount of fertilizer 25%.

It was further found that using 16 gallons GroAloe/ha can be used to reduce the amount of NPK chemical fertilizer by 25%. Further, it was found that these plants were not attacked by pests and diseases when GroAloe was used. Importantly, this study did not use chemical insecticides and/or fungicides. GroAloe has the effect of naturally repelling insects and has fungicidal properties that can be used also to control rice pests.

While GroAloe was less effective on plant growth, it provided significant increases in yield components (especially grain and grain total content) increased in number by giving GroAloe, so that the grain yield is also higher. Thus, GroAloe enriches the growth and yield of plants with additional materials such as macro- and micro-nutrients, humid acid, or beneficial soil bacteria. The present invention can find particular uses in soil conditions such at those found in Indonesia, China, Philippines and New Zealand.

These examples demonstrate that the present invention has a variety of uses, including: (1) increased moisture and nutrient uptake; (2) repels insects; (3) laboratory tested ability to kill bacteria, mold, yeast and fungus; (4) increase photosynthesis; (5) increase in plant production; (6) has no known toxicity after washing the plants, fruits, grasses or vegetables; and/or (7) does not harm the environment.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

Additionally, the section headings herein are provided for consistency with the suggestions under 37 CFR 1.77 or otherwise to provide organizational cues. These headings shall not limit or characterize the invention(s) set out in any claims that may issue from this disclosure. Specifically and by way of example, although the headings refer to a "Field of Invention," such claims should not be limited by the language under this heading to describe the so-called technical field. Further, a description of technology in the "Background of the Invention" section is not to be construed as an admission that technology is prior art to any invention(s) in this disclosure. Neither is the "Summary" to be considered a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings set forth herein.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A method for increasing the absorption of nutrients by rice plants to increase their growth comprising:
    identifying a plant in need of enhanced nutrient uptake and growth when compared to non-treated plants;
    providing the rice plant with an amount of a composition that consists of a whole leaf aloe vera extract diluted to 4 to 10% weight to volume phosphorous (P) and potassium (K); and
    at least one of mixing the whole leaf aloe vera extract into a plant growth media or spraying the whole leaf aloe vera extract on the plants, wherein the plant absorbs the one or more plant nutrients at a higher rate and the plants have at least one of increased growth, increased grain size, increased grain yield, increased yield, increased panicles, or an increase in the number of seedlings per plant when compared to the addition of the one or more nutrients alone.

2. The method of claim 1, wherein the aloe vera is a liquid, a gel, is dry, is ground, is freeze-dried, heat dried, vacuum dried, air-dried, spray-dried, or combinations thereof.

3. The method of claim 1, further comprising adding to the whole leaf aloe vera extract at least one of a stabilizer, an anti-oxidant, a water-repellent, a UV absorbing agent, an anti-microbial agent, or combinations thereof.

4. The method of claim 1, wherein the whole leaf aloe vera extract is added to the plant growth medium or sprayed on the plant in situ.

5. The method of claim 1, wherein the whole leaf aloe vera extract is added to the plant growth medium or sprayed on the plant at 8, 16, 24, 32, 48, 72, 80, 88, 96, or 120 liters per 10,000 $m^2$.

6. The method of claim 1, wherein the aloe vera gel comprises an aloin content at least 600, 800, 1,000, 2000 ppm or more.

7. The method of claim 1, wherein the increase plant growth or yield is achieved without the addition of pesticides or insecticides.

8. The method of claim 1, wherein the plant comprises a grass, a grain, a fruit or a vegetable.

9. The method of claim 1, wherein the whole leaf aloe vera extract is diluted to 9, 8, 7, 6, or 5 in a plant growth media or water prior to use.

10. The method of claim 1, wherein the plant growth media is selected from at least one of soil, nutrient enhanced soil, an in vitro growth media, hydroponic growth media, or agar growth media.

11. The method of claim 1, wherein the method further comprises reducing the amount of plant nutrients by 75, 50, or 25%, while still observing an increase in plant growth or yield.

12. A method for increasing the growth of a rice plant with a non-toxic, biodegradable composition comprising:
    identifying a plant growth media for growing rice that is low in one or more nutrients;
    mixing into the plant growth media or spraying on the rice a composition comprising an aloe vera extract diluted to between 4 to 6% weight to volume with the one or more nutrients selected from nitrogen (N), phosphorous (P), and potassium (K) that are missing from the plan growth media, such that the rice has increased growth, increased grain size, increased grain yield, increase in panicles, or an increase in the number of seedlings per rice plant, when compared to the addition of the one or more nutrients alone and without the need to treat the rice plants with an insecticide or a pesticide.

13. The method of claim 12, wherein the aloe vera extract is a liquid, gel, dry, ground, whole, freeze-dried, heat dried, vacuum dried, air-dried, spray-dried and combinations thereof.

14. The method of claim 12, further comprising adding to the aloe vera extract at least one of a stabilizer, anti-oxidant, a water-repellent, a UV absorbing agent, an anti-microbial agent, or combinations thereof.

15. The method of claim 12, wherein the plant growth media, the aloe vera extract and the one or more nutrients are mixed or sprayed in situ.

16. The method of claim 12, wherein the plant comprises a fruit or vegetable and wherein the fruit or vegetable has an increase in the size and number of fruit or vegetable size, fruit or vegetable number and combinations thereof.

17. The method of claim 12, wherein the plant comprises a grass, a grain, a fruit, a vegetable, or a tree.

18. The method of claim 12, wherein the aloe vera extract is added to the plant growth medium or sprayed on the plant at 8, 16, 24, 32, 48, 72, 80, 88, 96, or 120 liters per 10,000 m$^2$.

19. The method of claim 12, wherein an amount of nutrients are N, P, and K fertilizer is decreased by 25, 50, or 75 percent, while still observing an increase in plant growth or yield as a result of the mixing or spraying of the aloe vera extract.

\* \* \* \* \*